United States Patent
Itoh et al.

(10) Patent No.: US 9,890,412 B2
(45) Date of Patent: Feb. 13, 2018

(54) METHOD FOR QUANTIFYING SUBFRACTION OF CHOLESTEROL (–C) IN HIGH-DENSITY LIPOPROTEIN (HDL)

(71) Applicants: Denka Seiken Co., Ltd., Chuo-ku, Tokyo (JP); National University Corporation Hokkaido University, Kita-ku, Sapporo-shi, Hokkaido (JP)

(72) Inventors: Yasuki Itoh, Niigata (JP); Hitoshi Chiba, Hokkaido (JP)

(73) Assignees: Denka Seiken Co., Ltd., Tokyo (JP); National University Corporation Hokkaido University, Hokkaido (JP)

(*) Notice: Subject to any disclaimer, the term of this patent is extended or adjusted under 35 U.S.C. 154(b) by 385 days.

(21) Appl. No.: 14/391,897

(22) PCT Filed: Apr. 10, 2013

(86) PCT No.: PCT/JP2013/060778
§ 371 (c)(1),
(2) Date: Oct. 10, 2014

(87) PCT Pub. No.: WO2013/154119
PCT Pub. Date: Oct. 17, 2013

(65) Prior Publication Data
US 2015/0079616 A1    Mar. 19, 2015

(30) Foreign Application Priority Data
Apr. 11, 2012 (JP) ................................. 2012-090423

(51) Int. Cl.
*C12Q 1/60* (2006.01)
*G01N 33/92* (2006.01)

(52) U.S. Cl.
CPC ............... *C12Q 1/60* (2013.01); *G01N 33/92* (2013.01); *G01N 2333/775* (2013.01)

(58) Field of Classification Search
None
See application file for complete search history.

(56) References Cited

U.S. PATENT DOCUMENTS

| | | | |
|---|---|---|---|
| 5,691,159 A | 11/1997 | Miyauchi et al. | |
| 5,736,406 A | 4/1998 | Miyauchi et al. | |
| 5,773,304 A | 6/1998 | Hino et al. | |
| 2002/0001819 A1 | 1/2002 | Matsui et al. | |
| 2005/0032141 A1 | 2/2005 | DiMagno et al. | |
| 2005/0037504 A1* | 2/2005 | DiMagno ................. C12Q 1/60 436/71 |
| 2005/0095658 A1 | 5/2005 | Matsui et al. | |
| 2007/0275429 A1 | 11/2007 | Abe et al. | |
| 2009/0263844 A1* | 10/2009 | Itoh ........................ G01N 33/92 435/19 |
| 2010/0035288 A1* | 2/2010 | Itoh .......................... C12Q 1/44 435/11 |
| 2012/0208219 A1 | 8/2012 | Itoh et al. | |

FOREIGN PATENT DOCUMENTS

| | | |
|---|---|---|
| EP | 1046716 A1 | 10/2000 |
| EP | 2495332 A1 | 9/2012 |
| JP | 07-301636 A | 11/1995 |
| JP | 08-131197 A | 5/1996 |
| JP | 08-201393 A | 8/1996 |
| JP | 2001-095600 A | 4/2001 |
| JP | 2005-046145 A | 2/2005 |
| JP | 2007-295935 A | 11/2007 |
| JP | 2007-325587 A | 12/2007 |
| WO | WO 98/26090 A1 | 6/1998 |
| WO | WO 2011/052550 A1 | 5/2011 |

OTHER PUBLICATIONS

Supplementary European Search Report dated Nov. 30, 2015, in EP 13775869.4.
Okada et al., "Direct Measurement of HDL Cholesterol: Method Eliminating Apolipoprotein E-Rich Particles," Journal of Clinical Laboratory Analysis, 2001, 15:223-229.

* cited by examiner

*Primary Examiner* — Taeyoon Kim
*Assistant Examiner* — Srikanth Patury
(74) *Attorney, Agent, or Firm* — Foley & Lardner LLP (57) ABSTRACT

Provided is a method for separately or simultaneously quantifying whole HDL-C and cholesterol in HDL subfractions: ApoE-Containing HDL-C and ApoE-deficient HDL-C. A method for enzymatically and separately quantifying cholesterol in the ApoE-deficient HDL comprising: adding a surfactant composed of a polyoxyethylene benzyl phenyl ether derivative to a test sample in a final concentration of 0.05 to 0.10%, reacting the test sample with cholesterol esterase and cholesterol oxidase, and quantifying hydrogen peroxide generated. A method for enzymatically and separately quantifying cholesterol in ApoE-Containing HDL comprising: adding a surfactant composed of a polyoxyethylene benzyl phenyl ether derivative so as to obtain a final concentration of 0.15 to 0.75%, reacting the test sample with cholesterol esterase and cholesterol oxidase, and quantifying hydrogen peroxide generated.

3 Claims, 4 Drawing Sheets

METHOD FOR QUANTIFYING SUBFRACTION OF CHOLESTEROL (-C) IN HIGH-DENSITY LIPOPROTEIN (HDL)

CROSS-REFERENCE TO RELATED APPLICATIONS

This application is a National Stage application of PCT/JP2013/060778, filed Apr. 10, 2013, which claims priority from Japanese application JP 2012-090423, filed Apr. 11, 2012.

TECHNICAL FIELD

The present invention relates to a method for quantifying a cholesterol (-C) subfraction of high-density lipoprotein (HDL).

BACKGROUND ART

HDL receives cholesterol from tissues including arteriosclerotic vascular wall. Thus HDL is involved in cholesterol efflux accumulated in cells and serves as a risk-preventing factor for various types of arteriosclerosis including coronary arteriosclerosis. The blood level of HDL is known to serve as a useful prognostic indicator for onset of arteriosclerosis.

HDL is a complex of a protein called apoprotein and a lipid component such as a phospholipid, cholesterol and a triglyceride. HDL can be classified into subfractions, ApoE-Containing HDL and ApoE-deficient HDL, based on difference in the content of apolipoprotein E (ApoE) which is one of the components of the complex. The ApoE-Containing HDL has not only a high removability of cholesterol but also an antiplatelet action and has attracted attention as a super-good lipoprotein among the HDLs. Recently, an inhibitory agent for a cholesterol ester transfer protein (CETP) involved in increasing HDL-C has been expected to serve as a lipid-disorder therapeutic agent next to statin. A CETP inhibitory agent is known to mainly increase particularly ApoE-Containing HDL among HDLs.

As a method for measuring HDL-C, for example, a method in which HDL is separated from other lipoproteins by ultra-centrifugation and then subjected to measurement of cholesterol, and a method in which HDL is electrophoretically is separated; a lipid is stained; and its intensity of emission color is measured, are known. However, either one of these methods requires a complicated operation and is unable to treat many specimens. Because of the problems, these methods are not practically used in daily work.

As a method for measuring HDL-C; there is a method in which lipoproteins other than HDL are aggregated by adding a precipitator to a specimen; the aggregates are centrifugally removed; and cholesterol in the supernatant containing only HDL separated is measured. In this method, the reactivity to an HDL subfraction is known to vary depending upon the type of precipitator to be used herein. In a method using a precipitator such as phosphotungstic acid-magnesium and dextran sulfate-magnesium and heparin-calcium, ApoE-Containing HDL is aggregated with lipoproteins such as VLDL and LDL and centrifugally removed as a precipitation fraction and thus cannot be measured as an HDL fraction. In contrast, in a method using heparin-manganese and polyethylene glycol (PEG), ApoE-Containing HDL is not aggregated and thus is measured as HDL. In any case, a method of measuring HDL by separating HDL with a precipitator is simple compared to the ultra-centrifugation method and the electrophoresis method; however, it has a problem. Since an operation of separating HDL by adding a precipitator is included, this method is not satisfactory in view of simpleness. In addition, relatively a large amount of specimen is required.

Recently, as a method of simply quantifying HDL-C, a method of quantifying HDL-C by an automatic analyzer without a pretreatment using a precipitator, is known. More specifically, a method of specifically trapping HDL-C in the presence of a clathrate compound such as cyclodextrin by using chemically modified cholesterol esterase and cholesterol oxidase (see Patent Literature 1); a method in which lipoproteins except HDL are formed into an aggregate or a complex and thereafter cholesterol in HDL is trapped by an enzymatic reaction (see Patent Literatures 2 and 3); and a method of using a surfactant specifically acting on HDL and having an HLB of 13 to 14 (see Patent Literature 4) are known.

CITATION LIST

Patent Literature

Patent Literature 1: JP Patent Publication (Kokai) No, 7-301636
Patent Literature 2: JP Patent Publication (Kokai) No, 8-131197
Patent Literature 3: JP Patent Publication (Kokai) No. 8-201393
Patent Literature 4: WO98/26090

SUMMARY OF INVENTION

Technical Problem

In the methods described above, HDL-cholesterol (HDL-C) (hereinafter, cholesterol is sometimes represented by -C) can be measured; however reactivity to an HDL subtraction differs. In considering subtractions of HDL, these methods have the following problem: both of ApoE-deficient HDL cholesterol (ApoE-deficient HDL-C) and ApoE-Containing HDL cholesterol (ApoE-Containing HDL-C) cannot be even partially measured or can be hardly measured, and therefore ApoE-deficient HDL-C and ApoE-Containing HDL-C cannot be separately quantified.

An object of the present invention is to provide a method for separately or simultaneously quantifying cholesterol in whole HDL-C and HDL subtractions such as ApoE-Containing HDL-C and ApoE-deficient HDL-C without requiring an intricate fractionation/separation operation.

Solution to Problem

The present inventors conducted inventive studies, and as a result, they found the following: reactivities of a surfactant composed of a polyoxyethylene benzyl phenyl ether derivative to HDL subtractions, ApoE-deficient HDL-C and ApoE-Containing HDL-C, vary depending upon the concentration of the surfactant; ApoE-deficient ApoE-Containing HDL-C and total HDL-C can be separately or simultaneously quantified by controlling the concentration of the surfactant reacting with ApoE-deficient HDL-C and ApoE-Containing HDL-C. By controlling the concentration of the surfactant, not only ApoE-Containing HDL-C and ApoE-deficient HDL-C can be separately measured, but also whole HDL-C (including ApoE-Containing HDL-C and ApoE-deficient HDL-C) can be measured. They further found that when measurement is performed by using an a general automatic analyzer using three reagents in three steps, ApoE-Containing HDL-C, ApoE-deficient HDL-C and whole HDL-C can be singly measured, or a combination of them, i.e., two or three of them can be simultaneously measured, by guiding cholesterol in lipoproteins except HDL out of the reaction system in the first step and changing the concentrations of the surfactant in a second reagent and a third reagent used in the subsequent second step and the third step, respectively.

Furthermore, they found that ApoE-Containing HDL-C can be measured by a general automatic analyzer using two reagents in two steps by guiding cholesterol in lipoproteins except ApoE-Containing HDL out of the reaction system with a first reagent involving the conditions of the first step and the second step, and subsequently measuring ApoE-Containing HDL-C with the second reagent. Based on the findings, the present invention was accomplished.

As described above, owing to the method of the present invention, ApoE-deficient HDL-C and ApoE-Containing HDL-C having large particle sizes in a test sample can be separately quantified and further whole HDL-C including these HDL-C subtractions can be quantified.

More specifically, the present invention is as follows.

[1] A method for enzymatically and separately quantifying cholesterol in ApoE-deficient HDL, including adding a surfactant composed of a polyoxyethylene benzyl phenyl ether derivative to a test sample in a final concentration of 0.05 to 0.10%, reacting the test sample with cholesterol esterase and cholesterol oxidase, and quantifying hydrogen peroxide generated.

[2] A method for enzymatically and separately quantifying cholesterol in ApoE-Containing HDL, including adding a surfactant composed of a polyoxyethylene benzyl phenyl ether derivative to a test sample so as to obtain a final concentration of 0.15 to 0.75%, reacting the test sample with cholesterol esterase and cholesterol oxidase, and quantifying hydrogen peroxide generated.

[3] A method including: adding a surfactant composed of a polyoxyethylene benzyl phenyl ether derivative to a test sample in a final concentration of 0.05 to 0.10%, reacting the test sample with cholesterol esterase and cholesterol oxidase, and quantifying hydrogen peroxide generated to enzymatically and separately quantify cholesterol in the ApoE-deficient HDL; and then adding the surfactant composed of an polyoxyethylene benzyl phenyl ether derivative so as to obtain a final concentration of 0.15 to 0.75%, reacting the test sample with cholesterol esterase and cholesterol oxidase, and quantifying hydrogen peroxide generated to enzymatically and separately quantify cholesterol in ApoE-Containing HDL.

[4] A method for measuring cholesterol in HDL subtraction, including (i) guiding cholesterol in lipoproteins except HDL in a test sample out of a reaction system, (ii) separating and quantifying cholesterol in ApoE-deficient HDL by the method according to [1], and (iii) enzymatically separating and quantifying cholesterol in ApoE-Containing HDL by the method according to [2].

[5] The method according to any one of [1] to [4], in which total HDL-cholesterol is quantified based on the quantification value of cholesterol in the ApoE-deficient HDL obtained by the method according to [1] and an quantification value of cholesterol in the ApoE-Containing HDL obtained by the method according to [2].

[6] The method according to any one of [1] to [5], in which cholesterol in the ApoE-deficient HDL, cholesterol in the ApoE-Containing HDL, and total HDL-cholesterol are simultaneously quantified by a general automatic analyzer using a single sample.

[7] A method for quantifying cholesterol in ApoE-Containing HDL, including adding a surfactant composed of a polyoxyethylene benzyl phenyl ether derivative to a test sample in a final concentration of 0.05 to 0.10%, reacting the test sample with cholesterol esterase and cholesterol oxidase, removing hydrogen peroxide generated to thereby guide cholesterol in HDL except the ApoE-Containing HDL out of a reaction system, subsequently adding the surfactant composed of a polyoxyethylene benzyl phenyl ether derivative so as to obtain a final concentration of 0.15 to 0.75%, reacting the test sample with cholesterol esterase and cholesterol oxidase and quantifying hydrogen peroxide generated to quantify cholesterol in the ApoE-Containing HDL.

The specification incorporates the content of Description and/or the drawings of Japanese Patent Application No. 2012-090423, from which the present application claims the priority.

Advantageous Effects of Invention

In the method of the present invention, ApoE-deficient HDL-C is measured by using a surfactant, which reacts with HDL, in a low concentration (a final concentration of 0.05 to 0.10%) to react one of HDL subtraction, ApoE-deficient HDL, alone; and, in a second step, another HDL subfraction, ApoE-Containing HDL alone is reacted by using the surfactant in a concentration range where the reactivity to ApoE-Containing HDL-C is high, more specifically, in a high concentration (a final concentration of 0.15 to 0.75%). According to the present invention in which quantification of ApoE-Containing HDL-C and ApoE deficient-C is completed as mentioned above, ApoE-deficient HDL-C and ApoE-Containing HDL-C having large particle sizes in a test sample can be separately quantified and thither whole HDL-C including these HDL-C subtractions can be quantified. Only ApoE-Containing HDL-C can be measured.

DESCRIPTION OF EMBODIMENTS

The present invention will be more specifically described below.

As cholesterol contained in a lipoprotein, an ester type cholesterol (cholesterol ester) and free cholesterol are known. The description of "cholesterol" alone in the specification includes both of them.

Lipoproteins are roughly divided into VLDL, LDL and HDL fractions. Of them, HDL is classified into subtractions: ApoE-Containing HDL and ApoE-deficient HDL based on difference of the ApoE content. Usually, the ApoE-Containing HDL contains ApoE in HDL; whereas the ApoE-deficient HDL does not contain ApoE. The reason why HDL is classified into ApoE-Containing HDL and ApoE-deficient HDL is because these lipoproteins act on arteriosclerosis in different mechanisms, and thus, they need to be measured separately. More specifically, the ApoE-Containing HDL, which has not only a strong cholesterol removability but also an antiplatelet action, serves as a good HDL. Also, a CETP inhibitor agent, which increases HDL-C and serves as a lipid disorder therapeutic agent, is known to increase mainly ApoE-Containing HDL. HDL having ApoE or containing a larger amount of ApoE is sometimes called as ApoE-rich HDL, which is also included as the ApoE-Containing HDL. Since the distribution of the content of ApoE within the HDL is continuous, ApoE-Containing HDL and ApoE-deficient HDL cannot be clearly distinguished based on the content of ApoE in lipoproteins; however, for example, if HDL is fractionated by chromatography based on the content of ApoE, as described later, a specific ApoE content is previously determined and then the ApoE-Containing HDL and ApoE-deficient HDL may be distinguished based on the predetermined content.

HDL is also classified into HDL2 and HDL3 depending upon difference in density. ApoE-Containing HDL2 and ApoE-Containing HDL3 different in ApoE content are present. Furthermore, among HDLs having a larger particle size, HDL, in which apolipoprotein A1 (ApoA1) commonly present in HDL is absent and a large number of ApoE molecules are contained, is known. This is also included in ApoE-Containing HDL. The diameters of lipoprotein particles vary depending upon the reporter; however, the diameter of VLDL particles is 30 nm to 80 nm (30 nm to 75 nm); whereas the diameter of LDL particles is 22 nm to 28 nm (19 nm to 30 nm) and the diameter of HDL particles is 7 to 10 nm. The specific gravities of VLDL, LDL and HDL are 1.006 or less, 1.019 to 1.063 and 1.063 to 1.21, respectively.

The method of the present invention is directed to measurement of cholesterol in ApoE containing HDL, cholesterol in ApoE-deficient HDL, and cholesterol in whole HDL including ApoE containing HDL and ApoE-deficient HDL.

The test sample to be subjected to the measurement by the method of the present invention is not limited as long as it may possibly contain a lipoprotein such as HDL, LDL, VLDL and CM. Examples of the test sample include, but not limited to, a body fluid such as the serum and blood plasma and a diluted body fluid.

The method of the present invention is usually performed by use of an automatic analyzer. The method of the present invention can be performed by two steps: a first step and a second step, or by three steps: a first step, a second step and a third step. As a method consisting two steps and a method consisting three steps, the following methods are exemplified and the following reactions occur in individual steps of the methods.

(1) A method consisting of two steps in which ApoE-deficient HDL-C is measured in a first step and ApoE-Containing HDL-C is measured in a second step.

(2) A method consisting of three steps in which lipoproteins (CM, VLDL, LDL) except HDL are guided out of a reaction system in a first step; ApoE-deficient HDL-C is measured in a second step; and ApoE-Containing HDL-C is measured in a third step. In the method (2), the total HDL-C is determined based on the second step and the third step. The method corresponds to the method described in Example 3 (described later).

(3) A method consisting of two steps in which lipoproteins (CM, VLDL, LDL, ApoE deficient HDL-C) except ApoE-Containing HDL-C are guided out of a reaction system in a first step; and the ApoE-Containing HDL-C is measured in a second step. The method corresponds to the method described in Example 4 (described later).

The details of the method (1) consisting of two steps are as follows.

In the first step, ApoE-deficient HDL-C is measured by using a surfactant within a concentration range where the reactivity to ApoE-deficient HDL is high, more specifically, within a low concentration (a final concentration of 0.05 to 0.10%); and in the second step, ApoE-Containing HDL-C is measured by using a surfactant within a concentration range where the reactivity to ApoE-Containing HDL is high, more specifically, within a high concentration (a final concentration of 0.15 to 0.75%). A reaction of ApoE-deficient occurs in the first step and a reaction of ApoE-Containing HDL-C occurs in the second step. The ApoE-deficient HDL-C concentration can be determined based on an increase in absorbance in the first step, and the ApoE-Containing HDL-C concentration can be determined based on an increase in absorbance in the second step. Furthermore, the total HDL-C concentration can be determined based on a total increase in absorbance in the first step and second step.

In this method, even if lipoproteins except HDL are present in a sample, the ApoE-deficient HDL-C concentration and ApoE-Containing HDL-C concentration can be determined, and further, the total HDL-C concentration can be determined.

To more specifically measure the ApoE-deficient HDL-C concentration and ApoE-Containing HDL-C concentration, lipoproteins except HDL can be guided out of a reaction system in advance, as described in the following methods (2) and (3).

The details of the method (2) consisting of three steps are as follows.

In the first step, lipoproteins except a measurement subject, such as CM, VLDL and LDL, are guided out of a reaction system. As a result, in the steps on and after the second step, HDLs including HDL subtractions such as ApoE-Containing HIM and ApoE-deficient HDL react. More specifically, cholesterol esterase is reacted with a test sample and the cholesterol generated is reacted in the presence of an enzyme having a reactivity to cholesterol, such as cholesterol oxidase or cholesterol dehydrogenase, and guided out of a reaction system. At this time, the reaction may be carried out in the presence of a predetermined surfactant having a reactivity to the lipoprotein that is to be guided out of the reaction system.

The phrase "cholesterol of a lipoprotein is guided out of a reaction system" refers to removing or aggregating cholesterol contained in the above lipoprotein and inhibiting cholesterol so as not to react in the later step, such that cholesterol contained in lipoproteins such as CM, VLDL and LDL as well as an HDL subfraction except a measurement subject does not affect quantification of the measurement subject, i.e., HDL-C or an HDL-C subfraction.

The "removing" refers to decomposing lipoprotein-cholesterol in a test sample to prevent detection of a decomposition product in the following step. As a method for removing lipoprotein-cholesterol, a method of decomposing hydrogen peroxide, which is generated by the action of cholesterol esterase and cholesterol oxidase, into water and oxygen by use of catalase, is mentioned. Furthermore, a hydrogen donor and hydrogen peroxide generated may be reacted with the help of peroxidase and converted into a colorless quinone; however, the method is not limited to these.

There is a case where a lipoprotein is blocked and not reacted with an enzyme. In this case, the cholesterol of the lipoprotein is guided out of a reaction system. The "block" herein refers to a phenomenon where a surfactant, etc. binds (protect) to a lipoprotein to prevent the reaction of an enzyme with the lipoprotein. For example, in the method (2), LDL does not react in any one of the steps from the first step to the third step. In this case, it is said that LDL is removed out of the reaction system.

In the second step, cholesterol esterase is reacted with a test sample in the presence of a surfactant having a reactivity to HDL including ApoE-Containing HDL and ApoE-deficient HDL serving as a measurement subject. The cholesterol generated is reacted in the presence of an enzyme having a reactivity to cholesterol, such as cholesterol oxidase or cholesterol dehydrogenase and hydrogen peroxide generated is converted in a quinone dye, which is measured based on absorbance. In this manner, the measurement subject can be enzymatically quantified.

Depending upon the concentration of the surfactant to be used, the reactivity of the surfactant to ApoE-deficient HDL and ApoE-Containing HDL varies. For example, as shown in Example 1, if the concentration of the surfactant is low (a final concentration of 0.05 to 0.10%), the reactivity to the ApoE-deficient HDL is high; whereas, the reactivity to the ApoE-Containing HDL is low. In contrast, if the concentration of the surfactant is high (0.15 to 0.75%), the surfactant shows a reactivity to not only the ApoE-deficient HDL but also the ApoE-Containing HDL. Accordingly, if the surfactant is used within the above low concentration range, the ApoE-deficient HDL alone reacts and thus, ApoE-deficient HDL-C alone can be quantified. The final concentration of the surfactant herein refers to the concentration of a surfactant in the entire reaction system of a step, in which the reagents to be added in the step are contained. For example, in the above method (2), in a case where a first reagent (180 μl) and a sample (several μl) are added in the first step; a second reagent (60 μl) in added in the second step; and a third reagent (60 μl) is added in the third step, if a surfactant (D1%) is contained in the second reagent and a surfactant (D2%) is contained in the third reagent, the final concentration of the surfactant in the second step when the second reagent is added can be represented by $(D1 \times \frac{1}{4})$ %; whereas the final concentration of the surfactant in the third step when the third reagent is added can be represented by $\{(D1 \times \frac{1}{4}) \times \frac{4}{5} + D2 \times \frac{1}{5}\}$%. Furthermore, in the above method (3), in a case where a first reagent (180 μl) and a sample (several μl) are added in the first step; and a second reagent (60 μl) in added in the second step; if a surfactant (D3%) is contained in the first reagent and a surfactant (D4%) is contained in the second reagent, the final concentration of the surfactant in the first step when the first reagent is added can be represented by D3%; whereas, the final concentration of the surfactant in the second step when the second reagent is added can be represented by $\{(D3 \times \frac{3}{4}) + D4 \times \frac{1}{4}\}$%.

In the third step, if a surfactant is used within the above high concentration range, ApoE-Containing HDL reacts and thus ApoE-Containing HDL-C can be quantified. At this time, in the second step, the surfactant reacts only with ApoE-deficient HDL-C and hydrogen peroxide generates depending upon the amount of ApoE-deficient HDL-C to produce a quinone dye. In the third step, if a high-concentration surfactant is used, ApoE-Containing HDL reacts and hydrogen peroxide is further generated depending upon the amount of ApoE-Containing HDL-C to produce a quinone dye. An increase in absorbance of a quinone dye produced by the reaction of ApoE-Containing HDL-C in the third step compared to the second step is determined as the amount of ApoE-Containing HDL-C. Furthermore, increases in absorbance of a quinone dye produced by the reactions between a surfactant and ApoE deficient HDL-C and ApoE-Containing HDL-C both in the second step and the third step are summed up to determine the amount of total HDL-C including ApoE-deficient HDL-C and ApoE-Containing HDL-C.

As described above, to specifically measure ApoE-deficient HDL-C and ApoE-Containing HDL-C, a step of guiding lipoproteins except a measurement subject, such as CM, VLDL and LDL, out of a reaction system can be added before the step of reacting and quantifying ApoE-deficient HDL-C and ApoE-Containing HDL-C. In this method, lipoproteins except HDL are guided out of a reaction system in the first step; the reaction of ApoE-deficient HDL-C occurs in the second step; and the reaction of ApoE-Containing HDL-C occurs in the third step. Based on an increase in absorbance in the second step, the concentration of ApoE-deficient HDL-C can be determined. Furthermore, based on an increase in absorbance in the third step, the concentration of ApoE-Containing HDL-C can be determined. Furthermore, based on a total increase in absorbance in the second step and the third step, the total HDL-C concentration can be determined.

In the present invention, a general automatic analyzer is used and reagents different in composition are used in the first step, second step and third step. The reagents to be used in the first step, second step, third step are referred to as a first reagent, a second reagent, and a third reagent, respectively. As described above, owing to the use of three types of reagents, a single test sample undergoes a series of reactions and ApoE-deficient HDL-C, ApoE-Containing HDL-C, and total HDL-C concentrations can be calculated by measuring absorbance.

As the general automatic analyzer, Hitachi 7180, TBA200FR, AU640, BM6050, etc. can be used.

The details of the method (3) consisting of two steps are as follows.

In the first step, cholesterol contained in lipoproteins (CM, VLDL, LDL, ApoE-deficient HDL-C) except ApoE-Containing HDL-C is guided out of a reaction system. In the above method (2), lipoproteins except a measurement subject, such as CM, VLDL and LDL, are guided out of a reaction system in the first step; however, in this method, further a surfactant may be used within the concentration range where reactivity to ApoE-deficient HDL-C is high, more specifically, within a low surfactant concentration range (a final concentration of 0.05 to 0.10%) in the first step. More specifically, in this method, cholesterol in lipoproteins except ApoE-Containing HDL-C is guided out of the reaction system. In the second step, ApoE-Containing HDL-C is measured. In measurement of ApoE-Containing HDL-C, a surfactant may be used within a high concentration range (0.15 to 0.75%) in the same manner as in the method (2). In this method, a quinone dye is produced depending upon the amount of ApoE-Containing HDL-C in the second step. The ApoE-Containing HDL-C can be quantified by measuring the absorbance of the quinone dye.

In this reaction, since the first reagent is used in the first step and the second reagent is used in the second step, ApoE-Containing HDL-C can be measured only by two reagents.

As mentioned above, in the step of measuring or guiding cholesterol of the HDL subfractions: ApoE-deficient HDL and ApoE-Containing HDL, out of a reaction system by reacting the cholesterol in the present invention, a surfactant that reacts with HDL is used. In the step of decomposing and quantifying ApoE-deficient HDL-C, the surfactant is preferably used in a low concentration. The concentration range is 0.05 to 0.10% and preferably 0.075 to 0.10% in terms of a final concentration, as mentioned above. In contrast, in the step of decomposing and quantifying ApoE-Containing HDL-C, the surfactant is preferably used in a high concentration. The concentration range is 0.15 to 0.75%, and preferably 0.15 to 0.5% in terms of a final concentration, as mentioned above.

In the method (2) consisting of three steps as mentioned above, a surfactant reacting with HDL may be used in a low concentration in the second step and used in a high concentration in the third step. In the method (3) consisting of two steps, a surfactant reacting with HDL is used in a low concentration in the first step and used in a high concentration in the second step. In the method (1) consisting of two steps, the surfactant may be used in a low concentration in the first step and used in a high concentration in the second step.

In the method of the present invention, a surfactant reacting with HDL containing ApoE-deficient HDL and ApoE-Containing HDL is used. As the surfactant reacting with HDL, a surfactant having a ratio of ApoE-Containing HDL reactivity/ApoE-deficient HDL reactivity of 0.7 or more and less than 1.3, is mentioned, and a surfactant having a ratio of ApoE-Containing reactivity/ApoE-deficient HDL reactivity of 0.8 or more and less than 1.2 is preferably mentioned. The reactivity of a surfactant to a lipoprotein herein can be evaluated based on the reactivity of cholesterol when cholesterol esterase and cholesterol oxidase are reacted with a lipoprotein in the presence of the surfactant. More specifically, for example, the reactivity of the surfactant to a lipoprotein can be measured by adding various surfactants each to the reagent to be reacted with the lipoprotein and performing measurement. The reaction amount of surfactant to ApoE-Containing HDL and the reaction amount of surfactant to ApoE-deficient HDL are obtained and then the ratio of them to the total cholesterol in each of the samples (hereinafter, refers to the rate of "ApoE-Containing HDL reactivity/ApoE-deficient HDL reactivity") may be obtained. In this manner, the rate of ApoE-Containing HDL reactivity/ApoE-deficient HDL reactivity can be calculated.

Examples of the surfactant reacting with HDL include anionic surfactants such as a sodium alkyl benzene sulfonate, and nonionic surfactants such as a polyoxyethylene monolaurate, a lauryl alcohol alkoxylate, a polyoxyethylene lauryl amine, a polyoxyethylene benzyl phenyl ether derivative, a polyoxyethylene polyoxypropylene block polymer having a molecular weight of less than 1700 and a polyoxyethylene nonyl phenyl ether having HLB of 13.0 or more and less than 14.5. As an amphoteric surfactant, an alkyldimethylamino acetic acid betain and an alkylcarboxymethylhydroxyethylimidazorium betain are preferable, and a polyoxyethylene benzyl phenyl ether derivative is particularly preferable.

Specific examples of the surfactant include anionic surfactants such as Newrex soft 60-N, Newrex powder F, Newrex paste H (all manufactured by NOF Corporation), NEOPELEX No. 1-F, NEOPELEX G-65, and Emal NC-35 (all manufactured by Kao Corp.); nonionic surfactants such as ADEKATOL LB70, ADEKATOL LB-103, DEKATOL LB-93 (all manufactured by ADEKA Corporation), DISPANOL K-3, nonion L-4, nonion MN-811, nonion NS-210, nonion NS-212, NYMEEN L-202, Pronon 102, Pronon 204 (all manufactured by NOP Corporation), NONIPOL 85, NONIPOL 95, NONIPOL 100, NONIPOL 120 (all manufactured by Sanyo Chemical Industries Ltd.) and EMULGEN B66 (manufactured by Kao Corp.); and amphoteric surfactants such as AMPHITOL 24B (manufactured by Kao Corp.), NISSANANON BF, NISSANANON GLM-R-LV and NISSANANON LG (all manufactured by NOF Corporation).

Of them, e.g., EMULGEN B66, is a polyoxyethylene benzyl phenyl ether derivative.

In the method of the present invention, to measure cholesterol in an HDL subtraction in a test sample, first, lipoproteins except HDL are guided out of a reaction system by removing it, as is in the above methods (2) and (3). A method of removing lipoproteins except HDL, a method of using catalase and a method of forming colorless quinone can be mentioned. More specifically, cholesterol esterase and cholesterol oxidase are reacted with a test sample in the absence of a surfactant reacting to HDL and hydrogen peroxide generated from the lipoproteins except HDL is removed. Owing to the action of cholesterol esterase, cholesterol ester in the lipoproteins is hydrolyzed to produce free cholesterol and a fatty acid. Subsequently, the generated free cholesterol and free cholesterol present from the beginning in the lipoproteins are oxidized by the action of cholesterol oxidase to produce cholestenone and hydrogen peroxide. Hydrogen peroxide generated is removed to remove the lipoproteins. As a method for removing hydrogen peroxide, a method in which catalase is reacted to decompose hydrogen peroxide into water and oxygen, a method in which hydrogen peroxide is converted into a colorless quinone by reacting with a phenol-based or aniline-based hydrogen donor compound such as DAOS (N-ethyl-N-(2-hydroxysulfopropyl)-3,5-dimethyoxyaniline), which reacts with hydrogen peroxide to produce a colorless quinone, due to the action of peroxidase, can be mentioned; however, the method is not limited to these.

The step of guiding lipoproteins except HDL out of a reaction system may be performed in the absence of a surfactant reacting to the HDL. In this manner, HDL is virtually not reacted and lipoproteins such as LDL, VLDL-CM alone react. In this manner, cholesterol in other lipoproteins such as LDL, VLDL-CM alone is removed or protected and guided out of a reaction system. As a result, in the following second step, total HDL or cholesterol in an HU subtraction: ApoE-Containing HDL and/or ApoE-deficient HDL, can be selectively quantified by using a surfactant reacting with the HDL.

In the above methods (2) and (3), in the step of guiding lipoproteins except HDL out of a reaction system, or in the first step of guiding lipoproteins except ApoE-Containing HDL-C out of a reaction system, the concentration of cholesterol esterase in the reaction solution is preferably about 0.2 to 1.01 U/ml and the concentration of cholesterol oxidase is preferably about 0.1 to 0.7 U/ml. Furthermore, the concentration of catalase is preferably about 40 to 100 U/ml and the concentration of peroxidase is preferably about 0.4 to 1.0 U/ml. Furthermore, the concentration of a compound producing a colorless quinone through a reaction with hydrogen peroxide is preferably about 0.4 to 0.8 mmol/l.

In the above methods (2) and (3), the reaction of the first step is preferably performed in a buffer of pH5 to 8. As the buffer, phosphoric acid, glycine, Tris and are Good's buffers are preferable. Particularly, a Good's buffer such as Bis-Tris, PIPES, MOPSO, BES, HEPES and POPSO, is preferable. The concentration of the buffer is preferably about 10 to 500 mM.

In the first step of the above methods (2) and (3), to improve removal rate of lipoproteins except HDL, a divalent metal ion may be added to the reaction solution. As the divalent metal ion, a copper ion, ferrous ion and magnesium ion can be preferably used. Of them, particularly a magnesium ion is preferable. The concentration of the divalent metal ion is preferably about 5 to 200 mM. For example, magnesium chloride may be added.

Furthermore, to the reaction solution in the first step of the above methods (2) and (3), a lipoprotein hydrolytic enzyme may be optionally added. The addition of the enzyme is preferable since cholesterol can easily react particularly in VLDL. The concentration of the enzyme in the reaction solution is preferably about 5.0 to 10.0 U/ml.

The reaction temperature of each of the steps in the above methods (1), (2) and (3) is appropriately about 25° C. to 40° C. and most preferably, 37° C. Furthermore, the reaction time may be about 2 to 10 minutes.

The enzymatic quantification method itself of cholesterol produced in the method of the present invention is commonly known in the art, and can be performed, for example, in the same manner as in the first step of the above methods (2) and (3), by generating hydrogen peroxide by the action of cholesterol esterase and cholesterol oxidase from a cholesterol ester and free cholesterol and quantifying the hydrogen peroxide generated. The quantification of hydrogen peroxide can be performed, for example, by reacting hydrogen peroxide with a compound, which reacts with hydrogen peroxide to form a quinone dye, in the presence of peroxidase, and measuring the amount of quinone dye produced based on absorbance measurement. The quinone dye can be formed, for example, by using hydrogen peroxide and 4-aminoantipyrine and a phenol based or aniline based hydrogen donor.

Examples of the aniline based hydrogen donor compounds among the hydrogen donor compounds, include N-(2-hydroxy-3-sulfopropyl)-3,5-dimethoxyaniline (HDAOS), N-ethyl-N-sulfopropyl-3-methoxyaniline (ADPS), N-ethyl-N-sulfopropylaniline (ALPS), N-ethyl-N-sulfopropyl-3,5-dimethoxyaniline (DAPS), N-sulfopropyl-3,5-dimethoxy aniline (HDAPS), N-ethyl-N-sulfopropyl-3,5-dimethylaniline (MAPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl)aniline (ALOS), N-ethyl-N-(2-hydroxy-3-sulfopropyl)-3,5-dimethoxyaniline (DAOS), N-ethyl-N-(2-hydroxy-3-sulfopropyl)-3,5-dimethylaniline (MAOS) and N-ethyl-N-(2-hydroxy-3-sulfopropyl)-3-methylaniline (TOOS) and N-sulfopropyl aniline (HALPS).

The concentration of the compound producing a quinone dye is not particularly limited; however, it is preferably 0.1 to 2.0 mM, and further preferably 0.5 to 1.5 mM relative to the whole reaction mixture, for example, in the case of 4-aminoantipyrine; and preferably 0.5 to 2.0 mmol/L in the case of phenolic based or aniline based hydrogen donor compound. Furthermore, the concentration of peroxidase is not particularly limited; however, it is preferably 0.4 to 5 U/ml relative to the whole reaction mixture, Note that preferable reaction conditions (reaction temperature, reaction time, a buffer solution, pH) for the step of forming a quinone dye are the same as preferable reaction conditions for the step of guiding lipoproteins except HDL out of a reaction system or those for the step of guiding a lipoprotein except ApoE-Containing HDL-C out of a reaction system.

Note that in the step of guiding lipoproteins except HIM, out of a reaction system or the step of guiding lipoproteins except ApoE-Containing HDL-C out of a reaction system, when the generated hydrogen peroxide is decomposed by catalase, since catalase must be inhibited in the later step of forming a quinone dye, catalase is inhibited in the second step, for example, by a catalase inhibitor such as sodium azide.

EXAMPLES

The present invention will be more specifically described by way of Examples; however, the present invention is not limited to Examples. Note that in the following Examples, "%" represents "wt %" unless otherwise specified.

Example 1

A reagent having the following composition was prepared in order to confirm the effect of a surfactant concentration on HDL subtraction measurement.

| First reagent | |
|---|---|
| BES buffer | pH 7.0, 100 mmol/l |
| HDAOS | 0.7 mmol/l |
| Cholesterol esterase | 1.4 U/ml |
| Cholesterol oxidase | 0.8 U/ml |
| Catalase | 600 U/ml |
| Magnesium chloride | 10 mmol/l |
| Second reagent | |
| BES buffer | pH 7.0, 100 mmol/l |
| 4-Aminoantipyrine | 4.0 mmol/l |
| Cholesterol oxidase | 2.4 U/ml |
| Peroxidase | 2.4 U/ml |
| Sodium azide | 0.1% |
| Surfactant (Polyoxyethylene benzyl phenyl derivative) | 0.2, 0.4, 0.6, 0.8, 1.0, 1.5, 2.0, 3.0% |

Using the second reagents prepared by varying the concentration of the surfactant in the range of 0.2 to 3.0%, a high HDL-C sample (Total HDL-C 195.8 mg/ml) containing ApoE-deficient HDL-C in a concentration 141.8 mg/ml was measured to obtain reactivity to ApoE-deficient HDL. To the sample (2.4 μl), the first reagent (180 μl) was added and the mixture was reacted at 37° C. for 5 minutes and then the second reagent (60 d) was reacted at 37° C. for 5 minutes. Absorbance of the reaction mixture was measured at a main wavelength/side wavelength=600 nm/700 nm and difference in absorbance was obtained. Then, cholesterol concentration was obtained from a calibration curve. The final concentration of the surfactant in the reaction solution was 0.05 to 0.75%. The same sample was measured by a phosphotungstic acid-dextran sulfate-magnesium precipitation method (PT-DS-Mg method) (BIOCHEMICAL MEDICINE AND METABOLIC BIOLOGY 46, 329-343 (1991)), which can measure ApoE-deficient HDL-C alone and cannot measure ApoE-Containing HDL-C, used as a comparative method.

If the volume of the sample is ignored since it is very small compared to the volume of the reagents. The volume ratio of the first reagent to the second reagent is 3:1. Accordingly, the final concentration of the surfactant when the second reagent containing the surfactant (C1%) is added, becomes C1×¼%. In this Example, the since the concentration of the surfactant in the second reagent is 0.2 to 3.0%, the final concentration becomes 0.05 to 0.75%.

Figure 1:
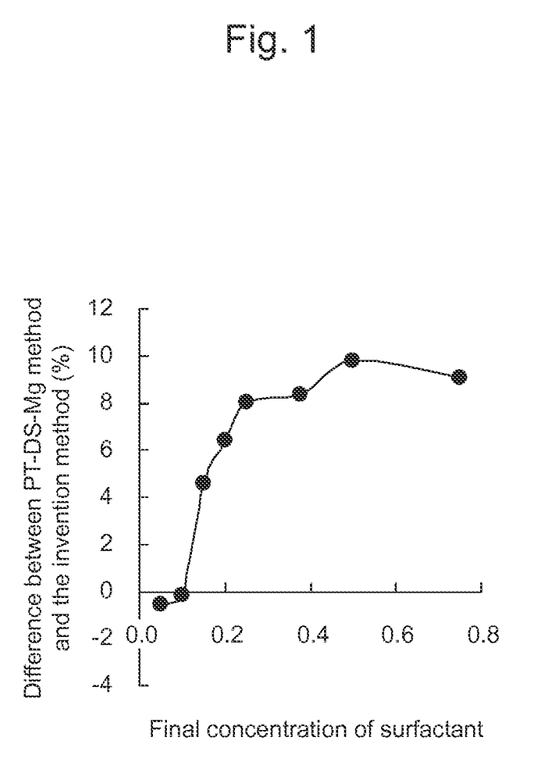
FIG. 1 is a graph showing difference (% bias) between the measurement value by the method for Example 1 of the present invention and that by the PT-DS-Mg method when an HDL sample is measured.

The results are shown in FIG. 1. FIG. 1 shows the results versus the final concentration of a surfactant are represented by % bias. The "% bias" can be obtained in accordance with the expression:

(measurement value in Example−measurement value by standard method)/measurement value by standard method×100.

As shown in FIG. 1, when the surfactant concentration of the second reagent is 0.2 to 0.4% (a final concentration: 0.05 to 0.10%), the % bias of the measurement value of a specimen having a high HDL-C value relative to that of the PT-DS-Mg method falls within the range of ±2%. In contrast, when the surfactant concentration of the second reagent is 0.6 to 3.0% (a final concentration: 0.15 to 0.75%), it is found that the measurement values are high and the surfactant reacts with an HDL subtraction (ApoE-Containing HDL-C) except ApoE-deficient HDL-C.

Example 2

A high HDL-C sample (total HDL-C, 195.8 mg/nil) was measured by using the same reagents and the same conditions as in Example 1. As a comparative method, a 13% PEG method (J Lipid Research 38, 1204-16: 1997) which can measure total HDL-C including ApoE-Containing HDL-C was used.

Figure 2:
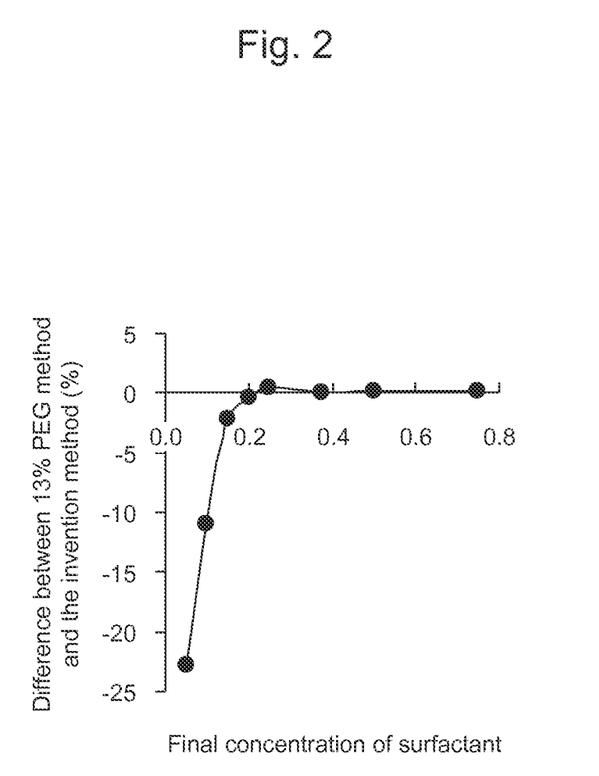
FIG. 2 is a graph showing difference (% bias) between the measurement value by the method for Example 2 of the present invention and that by the 13% PEG precipitation method when an HDL sample is measured.

The results are shown in FIG. 2. FIG. 2 shows the results versus the final concentration of a surfactant by % bias.

As shown in FIG. 2, when the surfactant concentration in the second reagent is 0.2 to 0.4% (a final concentration: 0.05 to 0.08%), the % bias of the measurement value of a specimen having a high HDL-C value relative to that of the 13% PEG method falls within the range of −2% or less. In contrast, when the surfactant concentration of the second reagent is 0.6 to 3.0% (a final concentration: 0.15 to 0.75%), the measurement values are high and % bias of the measurement value relative to that of 13% PEG method falls within ±2%. From this, it is found that the surfactant reacts with a total HDL-C including ApoE-Containing HDL-C in the presence of the surfactant in a high concentration.

Example 3

The first step (a first reagent is added) was specified as a step of guiding lipoproteins except an HDL out of a reaction system; the second step (a second reagent is added) as a step of measuring ApoE-deficient HDL-C; and the third step (a third reagent is added) as a step of measuring ApoE-Containing HDL-C, and the reagents to be used in these steps were prepared.

| First reagent | |
|---|---|
| BES buffer | pH 7.0, 100 mmol/l |
| HDAOS | 0.7 mmol/l |
| Cholesterol esterase | 1.4 U/ml |
| Cholesterol oxidase | 0.8 U/ml |
| Catalase | 600 U/ml |
| Magnesium chloride | 10 mmol/l |
| second reagent | |
| BES buffer | pH 7.0, 100 mmol/l |
| 4-Aminoantipyrine | 4.0 mmol/l |
| Peroxidase | 2.4 U/ml |
| Sodium azide | 0.1% |
| Surfactant (Polyoxyethylene benzyl phenyl derivative) | 0.2% |
| Third reagent | |
| BES buffer | pH 7.0, 100 mmol/l |
| Surfactant (Polyoxyethylene benzyl phenyl derivative) | 1.0% |

As an analysis apparatus, Hitachi 7180 was used. To the sample (2.4 µl), the first reagent (180 µl) was added and the mixture was reacted at 37° C. for 5 minutes, and then the second reagent (60 µl) was reacted at 37° C. for 5 minutes. Thereafter, the third reagent (60 µl) was reacted 37° C. for 5 minutes. Absorbance of the reaction mixture was measured in the conditions: main wavelength/side wavelength=600 nm/700 mm; measuring points: ApoE-deficient HDL-C: ApoE-Containing HDL-C: Δ27-22 and total HDL-C: Δ27-9, and difference in absorbance was obtained. The concentration of cholesterol (mg/dL) was calculated by multiplying a factor obtained by calibration. As comparative methods, the PT-DS-Mg method was used for measuring ApoE-deficient HDL-C, and the 13% PEG method was used for measuring total HDL-C including ApoE-Containing HDL-C. ApoE-Containing HDL-C was computationally obtained by subtracting the value obtained by the PT-DS-Mg method from the value obtained by the 13% PEG method. As samples, human sera different in HDL-C concentration were used.

The final concentration of the surfactant in the reaction solution having the second reagent added thereto was 0.2×¼=0.05%, whereas the final concentration of the surfactant in the reaction solution having the third reagent added thereto was 0.05×⅘+1.0×⅕=0.24%.

Figure 3:
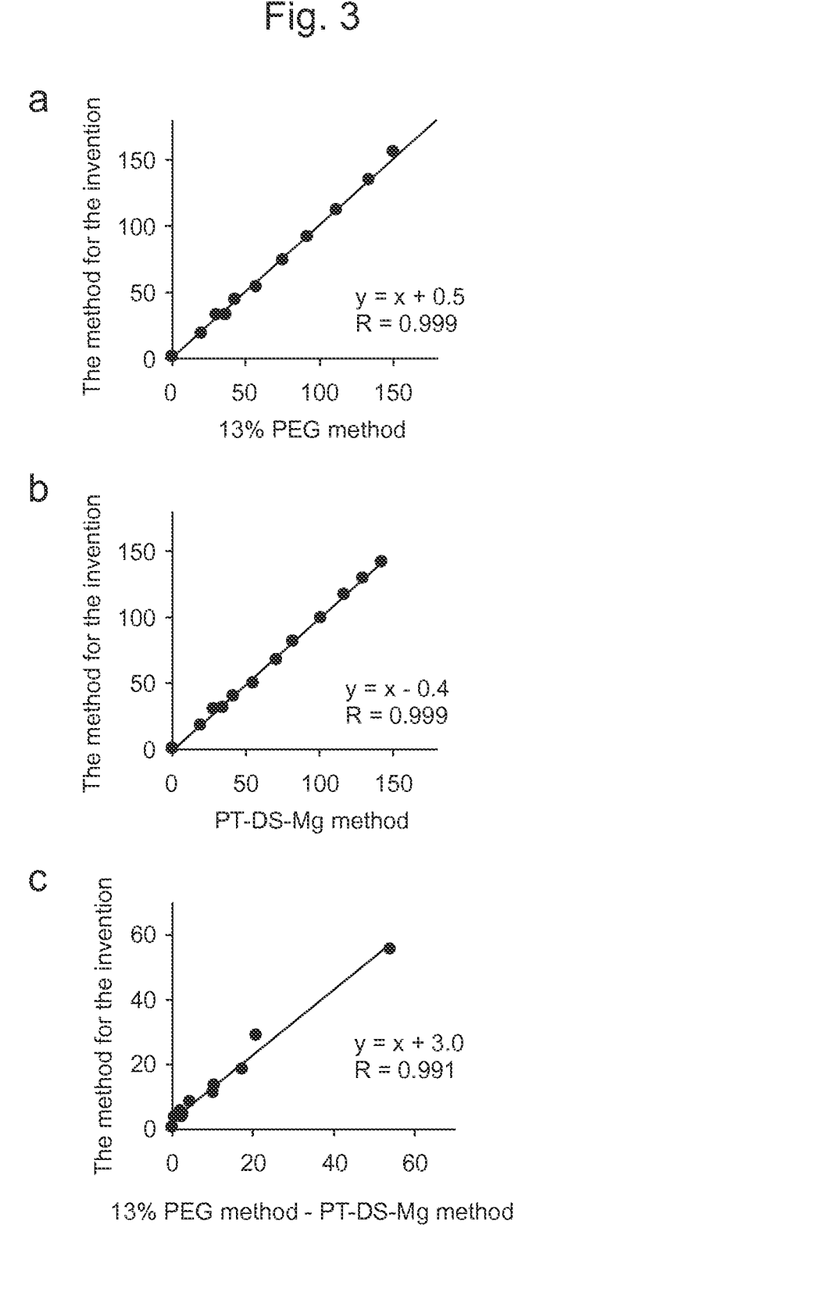
FIG. 3 is a graph showing the correlation between the method for Example 3 of the present invention and each of (a) the 13% PEG precipitation method, (b) the PT-DS-Mg precipitation method, and (c) difference between the 13% PEG precipitation method and the PT-DS-Mg precipitation method (all methods are applied to an HDL sample).

The results are shown in FIG. 3. FIG. 3 shows a correlation, between the measurement value obtained by the method of the present invention, and (a) the measurement value obtained by the 13% PEG precipitation method, (b) the measurement value obtained by the PT-DS-Mg precipitation method or (c) the difference between measurement values obtained by the 13% PEG precipitation method and the PT-DS-Mg precipitation method.

As shown in FIGS. 3a to c, the ApoE-deficient HDL-C, ApoE-Containing HDL-C and total HDL-C obtained by the method of the present invention each show a satisfactory correlation with the comparative method (y=x+0.5, r=0.999, y=x+0.4, r=0.991, y=x+3.0, r=0.999).

Example 4

The first step (first reagent is added) was specified as a step of guiding lipoproteins except ApoE-Containing HDL out of a reaction system; and the second step (second reagent is added) was specified as a step of measuring ApoE-Containing HDL-C, and the reagents to be used in these steps were prepared.

| First reagent | |
|---|---|
| BES buffer | pH 7.0, 100 mmol/l |
| HDAOS | 0.7 mmol/l |
| Cholesterol esterase | 0.8 U/ml |
| Cholesterol oxidase | 1.6 U/ml |
| Catalase | 600 U/ml |
| Magnesium chloride | 10 mmol/l |
| Surfactant (polyoxyethylene benzyl phenyl derivative) | 0.067% |

-continued

| Second reagent | |
| --- | --- |
| BES buffer | pH 7.0, 100 mmol/l |
| 4-Aminoantipyrine | 4.0 mmol/l |
| Peroxidase | 2.4 U/ml |
| Sodium azide | 0.1% |
| Surfactant (polyoxyethylene benzyl phenyl derivative) | 1.0% |

The same measurement conditions as in Example 1 were used here. More specifically, to the sample (2.4 μl), the first reagent (180 μl) was added and the mixture was reacted at 37° C. for 5 minutes, and then the second reagent (60 μl) was reacted at 37° C. for 5 minutes. Absorbance of the reaction mixture was measured at a main wavelength/side wavelength=600 nm/700 nm and the difference in absorbance was obtained. The concentration of cholesterol was obtained from a calibration curve. As a comparative method, ApoE-deficient HDL-C measurement method (PT-DS-Mg method) was used. As a comparative method, the PT-DS-Mg method and the 13% PEG method were used. The ApoE-Containing HDL-C concentration was computationally obtained by subtracting the value obtained by the PT-DS-Mg method from the value obtained by the 13% PEG method (both methods are comparative methods). As samples, human sera different in HDL-C concentration were used.

The final concentration of the surfactant in the reaction solution having the first reagent added thereto was 0.067% (sample volume was ignored since it was a small amount) and the final concentration of the surfactant in the reaction solution having the second reagent added thereto was 0.067× 415+1.0×⅕=0.254%.

Figure 4:
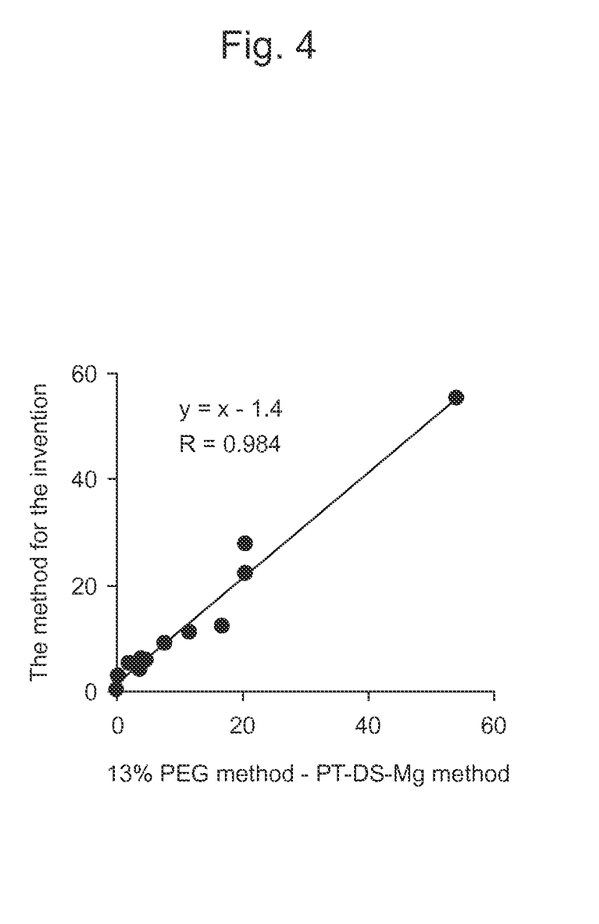
FIG. 4 is a graph showing the correlation between the method for Example 4 of the present invention and difference between the 13% PEG precipitation method and the PT-DS-Mg precipitation method (all methods are applied to an HDL sample).

The results are shown in FIG. 4. FIG. 4 shows correlations between the measurement value obtained by the method for Example 4 of the present invention and the difference between the value obtained by the 13% PEG precipitation method and the value obtained by the PT-DS-Mg method, As shown in FIG. 4, ApoE-Containing HDL-C obtained by the method of the present invention shows a satisfactory, correlation with the comparative method (y=x+1.4, r=0.984).

All publications and publications of patents and Japanese Patent Applications cited in the specification are incorporated herein in their entirety by reference.

The invention claimed is:

1. A method for quantifying cholesterol in ApoE-Containing HDL, comprising:
   (i) adding surfactant polyoxyethylene benzyl phenyl ether to a test sample in a final concentration of 0.05 to 0.10 wt %,
   reacting the test sample with cholesterol esterase and cholesterol oxidase, and
   removing cholesterol in HDL except the ApoE-Containing HDL; and
   (ii) subsequently adding the same surfactant used in step (i) so as to obtain a final concentration of 0.20 to 0.75 wt %, and
   reacting the test sample with cholesterol esterase and cholesterol oxidase, and
   quantifying hydrogen peroxide generated to quantify cholesterol in the ApoE-Containing HDL.

2. The method according to claim 1, wherein total HDL-cholesterol is quantified based on (i) the quantification value of cholesterol in the ApoE-deficient HDL obtained by adding surfactant polyoxyethylene benzyl phenyl ether to the test sample in a final concentration of 0.05 to 0.10 wt %, reacting the test sample with cholesterol esterase and cholesterol oxidase, and quantifying hydrogen peroxide generated; and (ii) a quantification value of cholesterol in the ApoE-Containing HDL obtained by adding the same surfactant as step (i) to the test sample so as to obtain a final concentration of 0.20 to 0.75 wt %, reacting the test sample with cholesterol esterase and cholesterol oxidase, and quantifying hydrogen peroxide generated.

3. The method according to claim 1, wherein cholesterol in the ApoE-deficient HDL, cholesterol in ApoE-Containing HDL, and total HDL-cholesterol are simultaneously quantified by a general automatic analyzer using a single sample.

* * * * *